(12) United States Patent
Lienhart et al.

(10) Patent No.: US 7,174,040 B2
(45) Date of Patent: Feb. 6, 2007

(54) FAST METHOD FOR TRAINING AND EVALUATING SUPPORT VECTOR MACHINES WITH A LARGE SET OF LINEAR FEATURES

(75) Inventors: Rainer W. Lienhart, Santa Clara, CA (US); Jochen Maydt, Weinheim (DE)

(73) Assignee: Intel Corporation, Santa Clara, CA (US)

( * ) Notice: Subject to any disclaimer, the term of this patent is extended or adjusted under 35 U.S.C. 154(b) by 647 days.

(21) Appl. No.: 10/199,744

(22) Filed: Jul. 19, 2002

(65) Prior Publication Data

US 2004/0015462 A1    Jan. 22, 2004

(51) Int. Cl.
*G06K 9/62* (2006.01)

(52) U.S. Cl. .............. 382/155; 382/224; 382/253; 382/276; 706/20

(58) Field of Classification Search ........... 382/224, 382/103, 159, 155, 253, 276; 706/12, 14, 706/15, 16, 19, 20, 21, 31, 41, 25, 45; 707/5; 708/323; 704/9

See application file for complete search history.

(56) References Cited

U.S. PATENT DOCUMENTS

| | | | | | |
|---|---|---|---|---|---|
| 5,950,146 | A | * | 9/1999 | Vapnik | 702/153 |
| 6,112,195 | A | * | 8/2000 | Burges | 706/20 |
| 6,134,344 | A | * | 10/2000 | Burges | 382/155 |
| 6,327,581 | B1 | * | 12/2001 | Platt | 706/12 |
| 6,658,395 | B1 | * | 12/2003 | Barnhill | 706/16 |
| 6,671,391 | B1 | * | 12/2003 | Zhang et al. | 382/118 |
| 6,803,933 | B1 | * | 10/2004 | Staelin et al. | 347/131 |
| 6,882,990 | B1 | * | 4/2005 | Barnhill et al. | 706/16 |

* cited by examiner

*Primary Examiner*—Sheela Chawan
(74) *Attorney, Agent, or Firm*—Sanjay S. Gadkari

(57) ABSTRACT

A procedure for fast training and evaluation of support vector machines (SVMs) with linear input features of high dimensionality is presented. The linear input features are derived from raw input data by means of a set of m linear functions defined on the k-dimensional raw input data. Training uses a one-time precomputation on the linear transform matrix in order to allow training on an equivalent training set with vector size k instead of m, given a great computational benefit in case of m>>k. A similar precomputation is used during evaluation of SVMs, so that the raw input data vector can be used instead of the derived linear feature vector.

44 Claims, 3 Drawing Sheets

FAST METHOD FOR TRAINING AND
EVALUATING SUPPORT VECTOR
MACHINES WITH A LARGE SET OF
LINEAR FEATURES

FIELD OF THE INVENTION

The present invention relates to computer mediated object detection. More particularly, the present invention relates to improved support vector machines for classifying data.

BACKGROUND

Any machine learning algorithm for classification/regression highly depends on the type and quality of the feature set. A feature set should ideally reduce intra-class variance and still be highly discriminative. Generally, it is desirable to use a rather small set of features to avoid dimensionality related problems and to speed up training and classification. Due to their simplicity, it is quite common to use linear features as the input to a classifier. There is a variety of powerful analysis methods, which derive linear features from raw input data including principal component analysis, Fisher discriminant analysis, Fourier transforms, Sobel-gradients, wavelets, and haar-likes.

Support vector machines (SVMs) are a class of learning algorithms for classification/regression that are particularly useful for high dimensional input data with either large or small training sets. Support vector machines suitable for class identification problems work by mapping the input features to the SVM into a high-dimensional feature space and computing linear functions on those mapped features in the high-dimensional feature space. The optimization problem that must be solved during training of a support vector machine has a global minimum and can generally be solved with standard quadratic programming tools. In operation, a support vector machine creates a function from a set of labeled training data. The function can either be a classification function where the output is a binary decision (the input being a category) or the function can be a general regression function. For classification, support vector machines operate by finding a hypersurface in the feature space (of the SVM). This hypersurface will attempt to split the positive examples from the negative examples. The split will be chosen to have the largest distance from the hypersurface to the nearest of the positive and negative examples, generally making the classification correct for testing data that is near, but not identical to the training data.

There are two simple conventional methods to train and evaluate a support vector machine using linear input features. The first method caches all linear feature vectors $z_i = Ax_i$, (i.e., it pre-computes the linear features $z_i$; $x_i$ denotes the raw input data of training sample i, and A is a matrix specifying all the linear features that are to be derived from the input data $x_i$.) and then uses these vectors to calculate kernel elements $K(z_i, z_j)$. Evaluation of a classifier then simply transforms an input pattern x to $z=Ax$ and uses $K(z, z_i)$ in $$\text{class}(x) = \text{sign}\left[\left(\sum_{i=1}^{n} y_i \alpha_i K(z, z_i)\right) + b\right] = \text{sign}\left[\left(\sum_{i=1}^{n} y_i \alpha_i K(Ax, z_i)\right) + b\right]$$

where $\alpha_i$ is the optimal solution of the maximization problem, b the associated threshold, and $y_i \in \{-1,+1\}$ the pattern label of support vector i.

For a large number of linear features (e.g., larger than a few thousand) it is usually not possible to store all vectors $z_i$ in memory, either for training or for evaluation. For instance, assuming a derivation of 250,000 linear features from each input data of dimension k<<250,000, a single feature vector may require more than one megabyte of memory storage making training sets with n>1,000 prohibitively expensive with present day computational resources.

Alternatively, to conserve memory, the function $z_i = Ax_i$ can be computed each time a kernel element $K((z_i, z_j)$ is accessed. This requires only storage of the original training examples $x_i$. Evaluating a classifier then computes $z=Ax$ and $z_i = Ax_i$ for each support vector i. However, this method is computationally very expensive because training a support vector machine needs many evaluations of the kernel function. Even with a kernel cache, far more than $10^6$ kernel evaluations to train a classifier on a training set may be required.

BRIEF DESCRIPTION OF THE DRAWINGS

The inventions will be understood more fully from the detailed description given below and from the accompanying drawings of embodiments of the inventions which, however, should not be taken to limit the inventions to the specific embodiments described, but are for explanation and understanding only.

DETAILED DESCRIPTION

Figure 1:
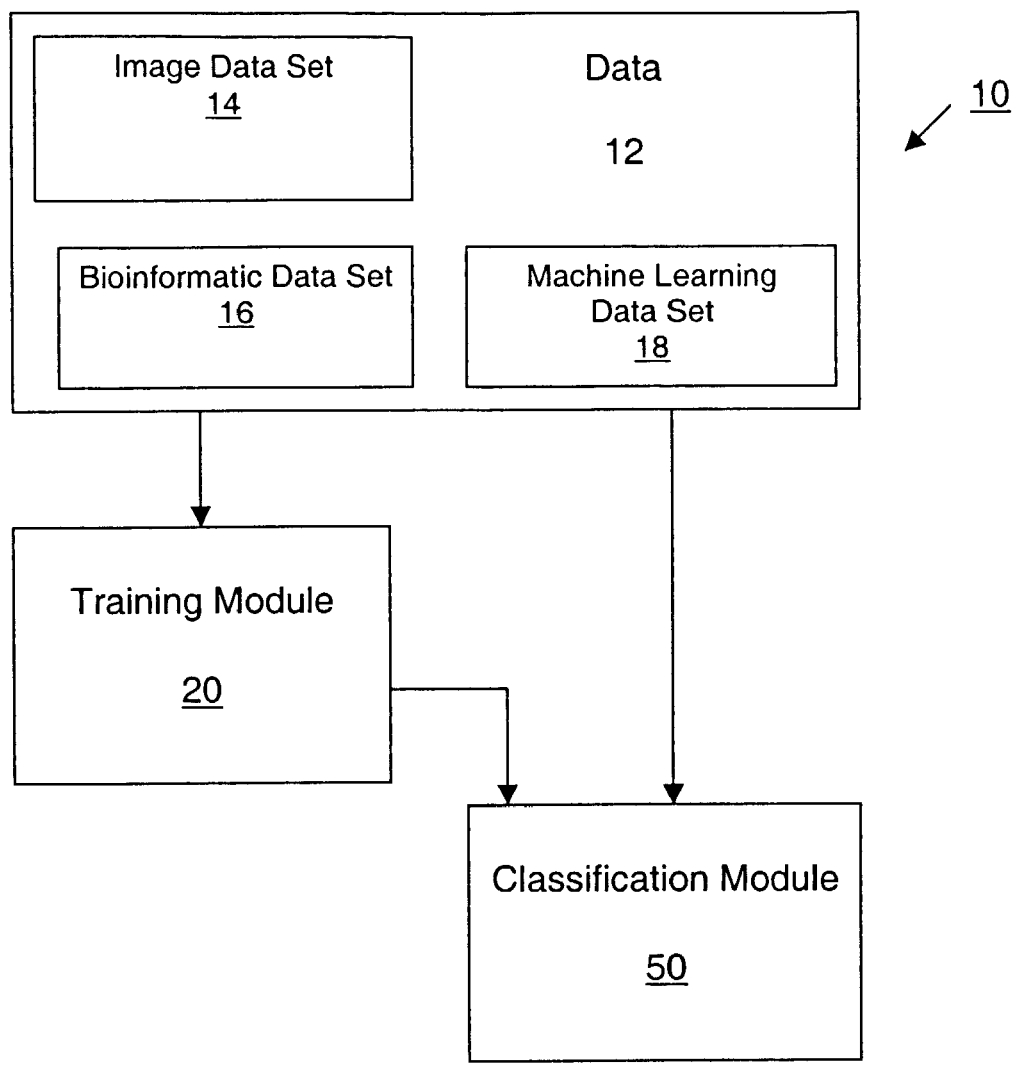
FIG. 1 schematically illustrates software module logic flow for an implementation of a fast support vector machine.

FIG. 1 illustrates a general system 10 for high speed data analysis of large data sets using a support vector machine. Such data sets 12 can include static or video imagery 14 containing objects to be identified or classified; bioinformatic databases 16 containing, for example, gene or protein sequences, DNA microarray data, sequence data, phylogenetic information, promoter region information; or textual, linguistic, or speech analysis data suitable for machine learning/identification 18. The same data set can be optionally used both to train and classify data with the appropriate training module 20 and classification module 50, or alternatively, a novel data set can be classified after training on data set 12. For example, speech data derived from a small number of persons can be used to train for machine identification of particular words from a large population of users.

The processing procedure for system 10 may be performed by a properly programmed general-purpose computer alone or in connection with a special purpose computer. Such processing may be performed by a single platform or by a distributed processing platform. In addition, such processing and functionality can be implemented in the form of special purpose hardware, custom application specific integrated circuits (ASICs), configurable FPGA circuits, or in the form of software or firmware being run by a general-purpose or network processor. Data handled in such processing or created as a result of such processing can be stored in any memory as is conventional in the art. By way of example, such data may be stored in a temporary memory, such as in the RAM of a given computer system or subsystem. In addition, or in the alternative, such data may be stored in longer-term storage devices, for example, magnetic disks, rewritable optical disks, and so on. For purposes of the disclosure herein, a computer-readable media may comprise, any form of data storage mechanism, including such existing memory technologies as well as hardware or circuit representations of such structures and of such data.

A support vector machine is used because it has good generalization performance even for high dimensional input data and small training sets. This makes them a method of choice for many binary classification tasks. A support vector machine solves the following quadratic program:

$$\max_{\alpha_i} \sum_{i=1}^{n} \alpha_i - \frac{1}{2} \sum_{i=1}^{n} \sum_{j=1}^{n} y_i y_j \alpha_i \alpha_j K(x_i, x_j)$$

$$\text{subject to } \sum_{i=1}^{n} y_i \alpha_i = 0, 0 \leq \alpha_i \forall i$$

where n is the number of training examples, $x_i \in R^k$ is the training example i and $y_i \in \{-1,+1\}$ is the class of $x_i$.

Other support vector machine formulations, e.g. with an $L_1$-norm error penalty C, are transparent to this method. Common kernel functions $K(x_i, x_j)$ are the linear kernel $K(x_i,x_j)=x_i^T x_j$, polynomial kernels $K(x_i,x_j)=(x_i^T x_j+c)^d$ of degree d, sigmoid kernels $K(x_i,x_j)=\tan h(x_i^T x_j+c)$ and radial basis function (RBF) kernels $K(x_i,x_j)=\exp(-\|x_i-x_j\|^2/c)$ with $c \in R$.

Computation speed during the support vector machine training procedure is improved by a one time pre-computation step. For example, if $A \in R^{m \times k}$ is the matrix that represents the linear transformation applied to the raw input data set to derive linear features, with vector size of the raw input data being k, with vector size of the linear features being m, and wherein $B := A^T A$, an upper triangular matrix $U \in R^{k \times k}$ such that $B = U^T U$ is determinable, and $x_i'' = U x_i$ for all $x_i$ of the training set is numerically calculated at improved speeds for k<m.

Figure 2:
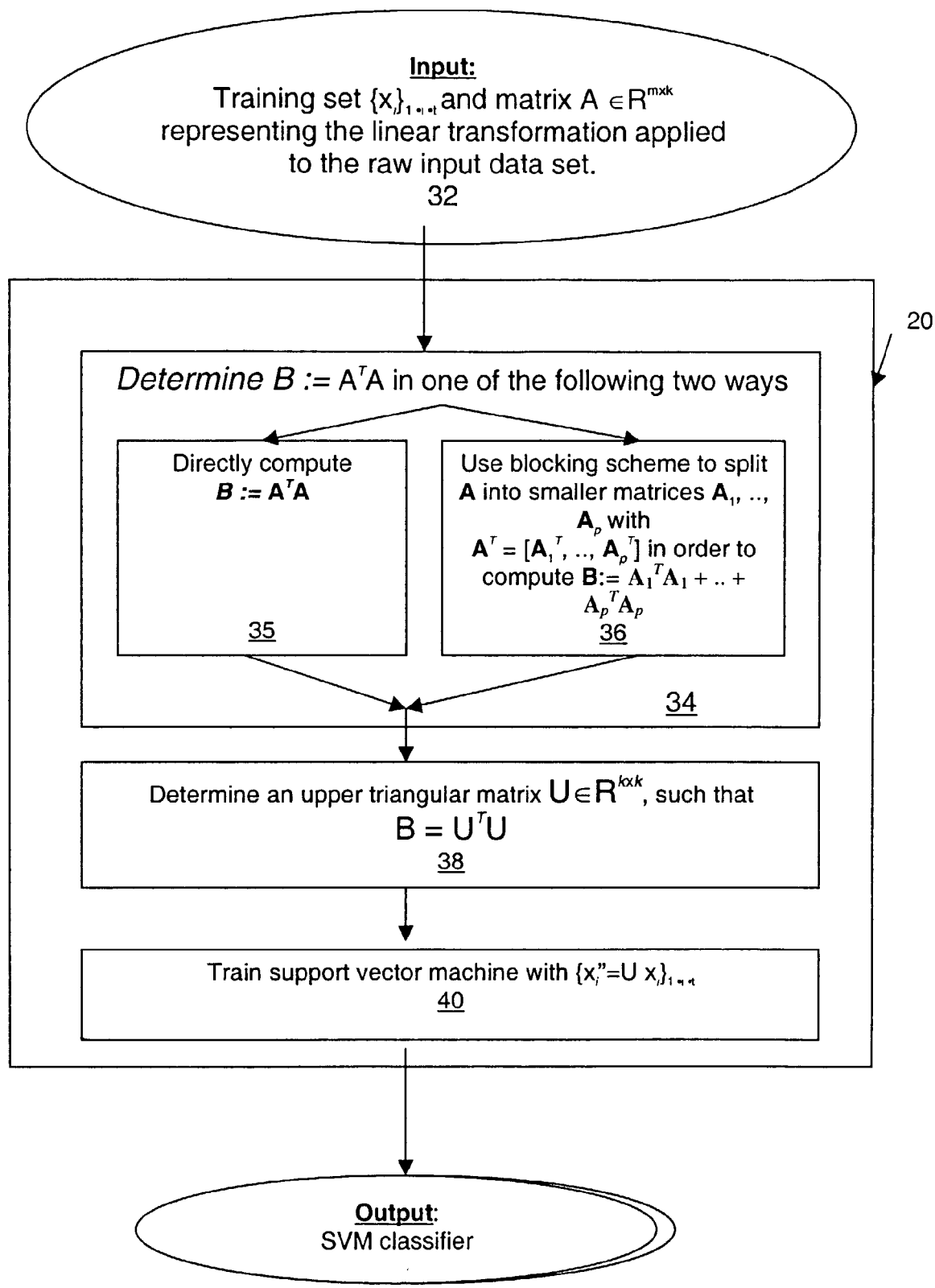
FIG. 2 more specifically illustrates a training procedure for a support vector machine with linear input features.

This can be seen with respect to FIG. 2, where a training software module and procedure 20 requires the linear transformation applied to the raw input data set to derive linear features as well as the raw training data as input (32), determines $B := A^T A$ (module 34), optionally optimized for available memory (module 36). Factorization of B results in upper triangular matrix $U \in R^{k \times k}$ (module 38) suitable for training such that $B = U^T U$.

More specifically, a linear kernel evaluation is determined as $$K(z_i, z_j)=z_i^T z_j=x_i^T A^T A x_j=x_i^T B x_j$$

where $B=A^T A$ is symmetric and $B \in R^{k \times k}$.

A Cholesky factorization of B results in $U^T U = B$ where $U \in R^{k \times k}$ is an upper triangular matrix. If a SVM is trained on $x_i''=U x_i$ instead of $z_i=A x_i$ the results of all kernel evaluations remain unchanged and the solution $\alpha_i$ is identical. However, there are several benefits of using $x_i'' \in R^k$ instead of $z_i \in R^m$:

1) evaluating a feature vector $z_i = Ax$ is not necessary.
2) $x_i''$ can usually be stored in memory as it is just as large as the original training data $x_i$.
3) For over-complete feature sets, i.e. m>k, the dot product $x_i''^T x_j''$ is of lesser complexity than $z_i^T z_j$.

Polynomial kernels $[(K(x_i,x_j)=(x_i^T x_j+c)^d$ of degree d] and sigmoid kernels $[K(x_i,x_j)=\tan h(x_i^T x_j+c)]$ also use the dot product $z_i^T z_j$ internally, allowing substitution of $K(z_i, z_j)$ with $K(x_i'', x_j'')$.

The same is true for RBF kernels $[K(x_i,x_j)=\exp(-\|^2 x_i-x_j\|^2/c)]$, as can be seen after a few reformulations. A simple reformulation of $\|z_i-z_j\|^2$ helps:

$$\|z_i - z_j\|^2 = \|A(x_i - x_j)\|^2$$
$$= (x_i - x_j)^T A^T A (x_i - x_j)$$
$$= (x_i - x_j)^T U^T U (x_i - x_j)$$
$$= \|U(x_i - x_j)\|^2$$
$$= \|U x_i - U x_j\|^2$$

and substituting $K(z_i, z_j)$ with $K(x_i'', x_j'')$ also can be used.

Since the optimal solution is still the same, the support vector machine can be trained alternatively with $x_i''$ instead of with $z_i = A x_i$.

In certain situations, straightforward implementation of this procedure is not possible because of hardware limitations. For example, A might be too large to fit into available computer memory (e.g., in our application A is typically larger than 100,000×1000, while B is only 500×500). However, a blocking scheme can be used to split A into smaller matrices $$A_1, \ldots, A_p \text{ with } A^T = [A_1^T, \ldots, A_p^T]$$

It follows that:

$$A^T A = [A_1^T, \ldots, A_p^T][A_1, \ldots, A_p]^T = A_1^T A_1 + \ldots + A_p^T A_p$$

Accordingly, B can be computed incrementally and only have to fit B and one of the smaller matrices into memory for each step.

To maintain numerical stability, double or greater precision calculations are generally required. Relative errors of 30% and more for the values of $K(x_i'', x_j'')$ can be encounter if single precision float values are used for A and B. Double precision floats usually provides enough significant digits and is more accurate than using $K(z_i, z_j)$ with single precision.

The Cholesky factorization $U^T U = B$ also introduces some numerical inaccuracy. It is possible to avoid it completely with a low additional memory overhead. If $x_i' = B x_i$, $x_i' \in R^k$ is computed (and keeping $x_i$ in memory as well) every kernel function can be expressed without referring to U. More exactly $K(z_i, z_j) = x_i^T x_j'$ for linear kernels and a similar result follows for polynomial and sigmoid kernels. For RBF kernels $s_i = x_i^T B x_i$ is storable and kernel evaluation is expressed as $$K(z_i, z_j) = K(x_i'', x_j'')$$
$$= \exp(-(x_i U^T U x_i - 2 x_i U^T U x_j + x_j U^T U x_j)/c)$$
$$= \exp(-(s_i - 2 x_i^T x_j' + s_j)/c).$$

Figure 3:
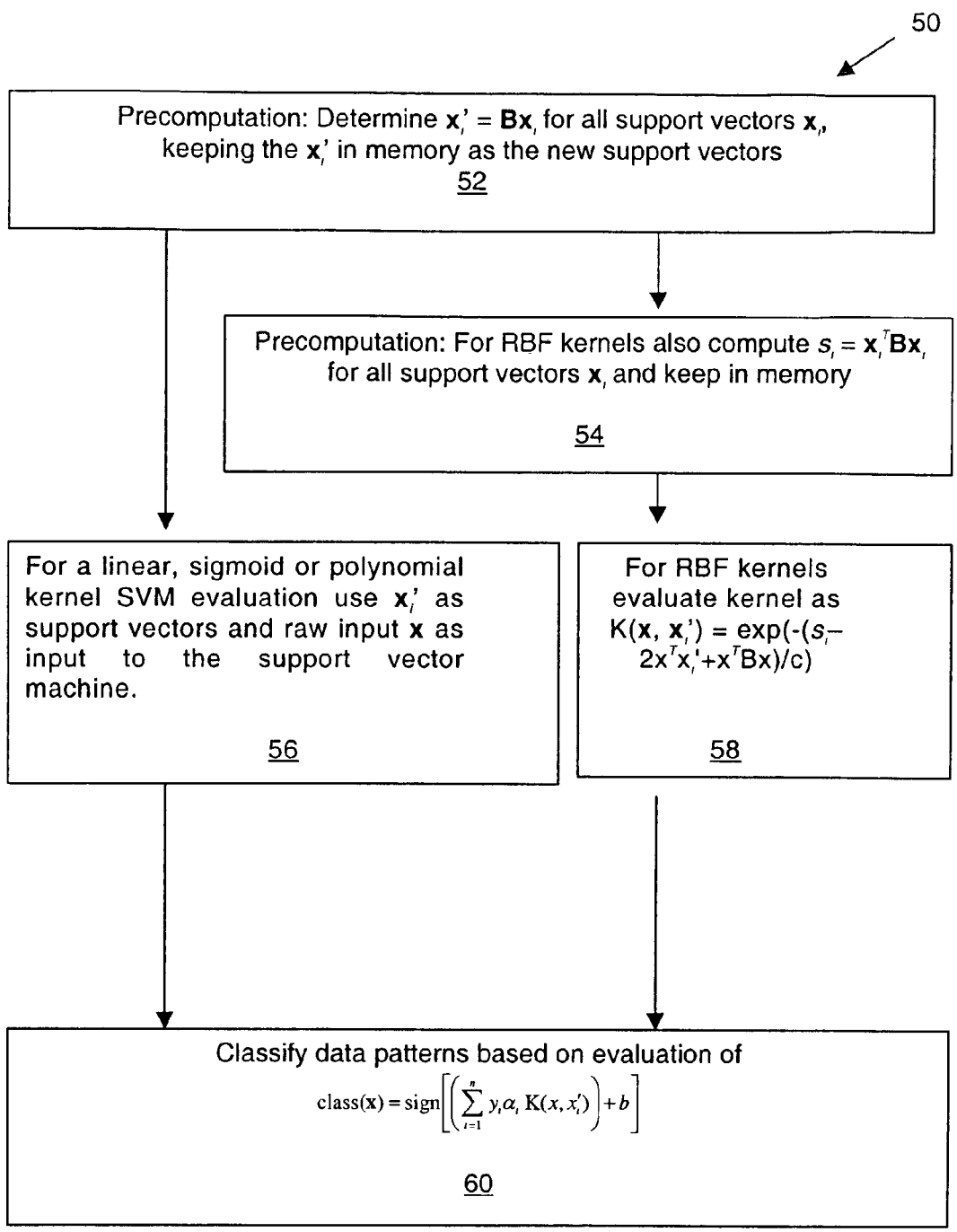
FIG. 3 more specifically illustrates an evaluation procedure of a trained support vector machine with linear input features.

Computation speed during evaluation of a trained support vector machine is also improved by a one-time pre-computation step for evaluation/classification of data sets. As seen in FIG. 3, an evaluation software module and procedure 50 requires determination (module 52) of $x_i'$ for all support vectors $x_i$, keeping the $x_i'$ in memory as the new support vectors. For linear kernels, $K(x,x_i')=x^T x_i'$ is determined (module 56), for polynomial kernels, $K(x,x_i')=(x^T x_i'+c)^d$ is determined, for sigmoid kernels, and $K(x,x_i')=\tan h(x^T x_i'+c)$ is determined (Note $K(z,z_j)=K(x,x_i')$.) The result is classified (module 60) For RBF kernels this procedure must be slightly modified as seen with respect modules 54 and 58 $[K(x, x_i')=\exp(-(s_i-2x^T x_i'+x^T Bx)/c)]$.

More specifically, the pre-computations requires determination of $x_i'=Bx_i$ for all support vectors $x_i$, keeping the $x_i'$ in memory as the new support vectors. For linear, polynomial and sigmoid kernels:

$$K((z, z_j)=K(x,x_i')$$

where $z=Ax$ and, thus, no linear features have to be evaluated.

For RBF kernels $$s_i = x_i^T B x_i$$

is also pre-computed for all support vectors $x_i$ and kept in memory. More specifically, RBF kernels are evaluated as:

$$K((x, x_i')=\exp(-(s_i-2x^T x_i'+x^T Bx)/c)$$

requiring linear feature evaluation of $x^T Bx$.

Computational complexity of classification mainly depends on three factors: feature evaluation, the dot product inside the kernel function and the number of support vectors. The evaluation scheme does not affect the number of support vectors. For m>>k classification is significantly faster, because dot product and feature evaluation are of lower complexity. For m≈k only feature evaluation is faster. This effect is almost negligible for high support vector counts.

Reference in the specification to "an embodiment," "one embodiment," "some embodiments," or "other embodiments" means that a particular feature, structure, or characteristic described in connection with the embodiments is included in at least some embodiments, but not necessarily all embodiments, of the invention. The various appearances "an embodiment," "one embodiment," or "some embodiments" are not necessarily all referring to the same embodiments.

If the specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

Those skilled in the art having the benefit of this disclosure will appreciate that many other variations from the foregoing description and drawings may be made within the scope of the present invention. Accordingly, it is the following claims including any amendments thereto that define the scope of the invention.

The claimed invention is:

1. A method to train a support vector machine for data classification comprising:

for some positive integers k, and m, and a feature data set comprising training samples (training data set), with the vector size of the raw input data of the training data set being k, the vector size of the linear features of each sample of the training data set being m, with m being greater than k, providing a one-time precomputation of the training data set to implicitly evaluate a linear kernel, the precomputation comprising a transformation in $R^{k \times k}$;

training a support vector machine with the precomputed data set and a defined kernel; and providing the trained support vector machine at least in part to perform data classification.

2. The method of claim 1, wherein $D \in R^{m \times n}$ is the matrix representing the training data set including n training samples.

3. The method of claim 1, wherein $A \in R^{m \times k}$ is the matrix representing a linear transformation applied to the raw input data set required to derive all linear features of the raw input data, wherein $B \in R^{k \times k}$ is determined by computing $B=A^T A$.

4. The method of claim 1, wherein $A \in R^{m \times k}$ is the matrix representing the linear transformation applied to the raw input data set, and wherein $B \in R^{k \times k}$ is determined by computing $B:=A^T A$ using a blocking scheme to split A into a set of smaller matrices.

5. The method of claim 1, wherein $A \in R^{m \times k}$ is the matrix representing the linear transformation applied to the raw input data set, and wherein $B \in R^{k \times k}$ is determined by computing $B:=A^T A$ using a blocking scheme to split A into a set of smaller matrices $A_1, \ldots, A_p$ with $A^T=[A_1^T, \ldots, A_p^T]$, for incremental computation of $B \in R^{k \times k}$.

6. The method of claim 1, wherein $A \in R^{m \times k}$ is the matrix representing the linear transformation applied to the raw input data set, wherein $B \in R^{k \times k}$ is determined by computing $B:=A^T A$; and an upper triangular matrix $U \in R^{k \times k}$ is determined such that $B=U^T U$.

7. The method of claim 1, wherein $A \in R^{m \times k}$ is the matrix representing the linear transformation applied to the raw input data set, wherein $B \in R^{k \times k}$ is determined by computing $B:=A^T A$; and Cholesky factorization is used to define an upper triangular matrix $U \in R^{k \times k}$ such that $B=U^T U$.

8. The method of claim 1, wherein $A \in R^{m \times k}$ is the matrix representing the linear transformation applied to the raw input data set, wherein $B \in R^{k \times k}$ is determined by computing $B:=A^T A$; an upper triangular matrix $U \in R^{k \times k}$ such that $B=U^T U$ is determined, and $x_i''=U x_i$ for all $x_i$ of the training set. $\{x_i''\}_{1 \leq i \leq t}$ represents the one-time precomputation in claim 1.

9. The method of claim 1, wherein the defined kernel is a linear kernel.

10. The method of claim 1, wherein the defined kernel is a sigmoid kernel.

11. The method of claim 1, wherein the defined kernel is a polynomial kernel.

12. The method of claim 1, wherein the defined kernel is a RBF kernel.

13. The method of claim 1, wherein the feature data set comprises images having identifiable objects.

14. The method of claim 1, wherein the feature data set comprises biological database information.

15. The method of claim 1, wherein the feature data set comprises machine learning database information.

16. The method of claim 1, wherein $A \in R^{m \times k}$ is the matrix representing the linear transformation applied to the raw input data set, and wherein $B \in R^{k \times k}$ is determined by computing $B:=A^T A$; an upper triangular matrix $U \in R^{k \times k}$ such that $B=U^T U$ is determined, and $x_i''=U x_i$ for all $x_i$ of the training set. $\{x_i''\}_{1 \leq i \leq t}$ represents the one-time precomputation.

17. An article comprising a storage medium having stored thereon instructions that when executed by a machine cause the machine to perform a method to train a support vector machine for data classification, the method comprising:

for some positive integers k, and m, and a feature data set comprising training samples (training data set), with the vector size of the raw input data of the training data set being k, the vector size of the linear features of each sample of the training data set being m, with m being greater than k, providing a one-time precomputation of the training data set to implicitly evaluate a linear kernel, the precomputation comprising a transformation in $R^{k \times k}$;

training a support vector machine with the precomputed data set and a defined kernel; and providing the trained support vector machine at least in part to perform data classification.

18. The article comprising a storage medium having stored thereon instructions according to claim 17, wherein $D \in R^{m \times n}$ is the matrix representing the training data set including n training samples.

19. The article comprising a storage medium having stored thereon instructions according to claim 17, wherein $A \in R^{m \times k}$ is the matrix representing the linear transformation applied to the raw input data set, and wherein $B \in R^{k \times k}$ is determined by computing $B := A^T A$.

20. The article comprising a storage medium having stored thereon instructions according to claim 17, wherein $A \in R^{m \times k}$ is the matrix representing the linear transformation applied to the raw input data set, and wherein $B \in R^{k \times k}$ is determined by computing $B := A^T A$ using a blocking scheme to split A into a set of smaller matrices.

21. The article comprising a storage medium having stored thereon instructions according to claim 17, wherein $A \in R^{m \times k}$ is the matrix representing the linear transformation applied to the raw input data set, and wherein $B \in R^{k \times k}$ is determined by computing $B := A^T A$ using a blocking scheme to split A into a set of smaller matrices $A_1, \ldots, A_p$ with $A^T = [A_1^T, \ldots, A_p^T]$, for incremental computation of $B \in R^{k \times k}$.

22. The article comprising a storage medium having stored thereon instructions according to claim 17, wherein $A \in R^{m \times k}$ is the matrix representing the data set, and wherein $B \in R^{k \times k}$ is determined by computing $B := A^T A$; and an upper triangular matrix $U \in R^{k \times k}$ is determined such that $B = U^T U$.

23. The article comprising a storage medium having stored thereon instructions according to claim 17, wherein $A \in R^{m \times k}$ is the matrix representing the linear transformation applied to the raw input data set, and wherein $B \in R^{k \times k}$ is determined by computing $B := A^T A$ is determined; and an upper triangular matrix $U \in R^{k \times k}$ is determined such that $B = U^T U$.

24. The article comprising a storage medium having stored thereon instructions according to claim 17, wherein $A \in R^{m \times k}$ is the matrix representing the linear transformation applied to the raw input data set, and wherein $B \in R^{k \times k}$ is determined by computing $B : A^T A$; an upper triangular matrix $U \in R^{k \times k}$ such that $B = U^T U$ is determined, and $x_i'' = U x_i$ for all $x_i$ of the training set. $\{x_i''\}_{1 \leq i \leq t}$ represents the one-time precomputation.

25. The article comprising a storage medium having stored thereon instructions according to claim 17, wherein the defined kernel is a linear kernel.

26. The article comprising a storage medium having stored thereon instructions according to claim 17, wherein the defined kernel is a sigmoid kernel.

27. The article comprising a storage medium having stored thereon instructions according to claim 17, wherein the defined kernel is a polynomial kernel.

28. The article comprising a storage medium having stored thereon instructions according to claim 17, wherein the defined kernel is a RBF kernel.

29. The article comprising a storage medium having stored thereon instructions according to claim 17, wherein the feature data set comprises images having identifiable objects.

30. The article comprising a storage medium having stored thereon instructions according to claim 17, wherein the feature data set comprises biological database information.

31. A system for improving speed of support vector machines comprising:

a software module providing for some positive integers k, and m, and a feature data set comprising training samples (training data set), with the vector size of the raw input data of the training data set being k, the vector size of the linear features of each sample of the training data set being m, with m being greater than k, a one-time precomputation of the training data set to implicitly evaluate a linear kernel, the precomputation comprising a transformation in $R^{k \times k}$; and a support vector machine trainable with the precomputed data set and a defined kernel.

32. The system of claim 31, wherein $D \in R^{m \times n}$ is the matrix representing the training data set including n training samples.

33. The system of claim 31, wherein $A \in R^{m \times k}$ is the matrix representing the linear transformation applied to the raw input data set, and wherein $B \in R^{k \times k}$ is determined by computing $B := A^T A$.

34. The system of claim 31, wherein $A \in R^{m \times k}$ is the matrix representing the linear transformation applied to the raw input data set, and wherein $B \in R^{k \times k}$ is determined by computing $B := A^T A$ using a blocking scheme to split A into a set of smaller matrices.

35. The system of claim 31, wherein $A \in R^{m \times k}$ is the matrix representing the linear transformation applied to the raw input data set, and wherein $B \in R^{k \times k}$ is determined by computing $B := A^T A$ using a blocking scheme to split A into a set of smaller matrices $A_1, \ldots, A_p$ with $A^T = [A_1^T, \ldots, A_p^T]$, for incremental computation of $B \in R^{k \times k}$.

36. The system of claim 31, wherein $A \in R^{m \times k}$ is the matrix representing the linear transformation applied to the raw input data set, and wherein $B \in R^{k \times k}$ is determined by computing $B := A^T A$; and an upper triangular matrix $U \in R^{k \times k}$ is determined such that $B = U^T U$.

37. The system of claim 31, wherein $A \in R^{m \times k}$ is the matrix representing the linear transformation applied to the raw input data set, and wherein $B \in R^{k \times k}$ is determined by computing $B := A^T A$; and Cholesky factorization is used to define an upper triangular matrix $U \in R^{k \times k}$ such that $B = U^T U$.

38. The system of claim 31, wherein the defined kernel is a linear kernel.

39. The system of claim 31, wherein the defined kernel is a sigmoid kernel.

40. The system of claim 31, wherein the defined kernel is a polynomial kernel.

41. The system of claim 31, wherein the defined kernel is a RBF kernel.

42. The system of claim 31, wherein the feature data set comprises images having identifiable objects.

43. The system of claim 31, wherein the feature data set comprises biological database information.

44. The system of claim 31, wherein the feature data set comprises machine learning database information.

* * * * *